United States Patent [19]

Peet et al.

[11] Patent Number: 5,256,650
[45] Date of Patent: Oct. 26, 1993

[54] SELECTIVE ADENOSINE RECEPTOR AGENTS

[75] Inventors: Norton P. Peet, Cincinnati; Nelsen L. Lentz, West Chester, both of Ohio

[73] Assignee: Merrell Dow Pharmaceuticals Inc., Cincinnati, Ohio

[21] Appl. No.: 954,178

[22] Filed: Sep. 30, 1992

Related U.S. Application Data

[63] Continuation-in-part of Ser. No. 873,660, Apr. 22, 1992, abandoned, which is a continuation of Ser. No. 734,024, Jul. 22, 1991, abandoned, which is a continuation of Ser. No. 551,686, Jul. 9, 1990, abandoned, which is a continuation of Ser. No. 329,919, Mar. 29, 1989, abandoned.

[51] Int. Cl.$^5$ .................. C07H 19/06; C07D 473/30; A61K 31/70
[52] U.S. Cl. .......................... 514/46; 514/45; 514/258; 514/261; 536/27.6; 536/27.61; 536/27.62; 536/27.63; 544/262; 544/277
[58] Field of Search ............... 536/27.6, 27.61, 27.62, 536/27.63; 544/277, 262; 514/45, 46, 261, 258

[56] References Cited

U.S. PATENT DOCUMENTS

| | | | |
|---|---|---|---|
| 3,211,732 | 10/1965 | Schmidt | 544/262 |
| 3,225,046 | 12/1965 | Zwahlen | 544/277 |
| 3,502,649 | 3/1970 | Thiel | 536/27.62 |
| 3,590,029 | 6/1971 | Koch | 536/27.62 |
| 3,862,189 | 1/1975 | Schwender | 544/277 |
| 4,388,308 | 6/1983 | Hamilton | 514/46 |
| 4,514,405 | 4/1985 | Irmscher | 514/46 |
| 4,853,386 | 8/1989 | Friebe | 544/277 |
| 4,904,666 | 2/1990 | Friebe | 544/262 |
| 5,043,325 | 8/1991 | Olsson | 514/46 |

FOREIGN PATENT DOCUMENTS 408945 9/1966 Switzerland .................. 544/262

*Primary Examiner*—C. Warren Ivy
*Assistant Examiner*—Celia Chay
*Attorney, Agent, or Firm*—Michael J. Sayles

[57] ABSTRACT

Adenosine analogues which act selectively at adenosine receptors and which act in general as adenosine antagonists are disclosed. From *in vitro* studies it is known that specific physiological effects can be distinguished as a result of this selectivity and that adenosine receptor activity *in vitro* correlates with adenosine receptor activity *in vivo*.

Pharmaceutical preparations of the subject compounds can be prepared on the basis of the selective binding activity of the compounds disclosed herein which will enhance certain physiological effects while minimizing others, such as decreasing blood pressure without decreasing heart rate.

11 Claims, No Drawings

SELECTIVE ADENOSINE RECEPTOR AGENTS

CROSS-REFERENCE TO RELATED APPLICATIONS

This is a continuation-in-part of application Ser. No. 07/873,660, filed Apr. 22, 1992, now abandoned, which is a continuation of application Ser. No. 07/734,024, filed Jul. 22, 1991, now abandoned, which is a continuation of application Ser. No. 07/551,686, filed Jul. 9, 1990, now abandoned, which is a continuation of application Ser. No. 07/329,919, filed Mar. 29, 1989, now abandoned.

FIELD OF THE INVENTION

The present invention relates to a group of compounds which are adenosine analogues and which act selectively at adenosine receptors.

BACKGROUND OF THE INVENTION

The profound hypotensive, sedative, antispasmodic, and vasodilatory actions of adenosine were first recognized over 50 years ago. Subsequently, the number of biological roles proposed for adenosine have increased considerably. The adenosine receptors appear linked in many cells to adenylate cyclase. A variety of adenosine analogues have been introduced in recent years for the study of these receptor functions. Alkylxanthines, such as caffeine and theophylline, are the best known antagonists of adenosine receptors.

Adenosine perhaps represents a general regulatory substance, since no particular cell type or tissue appears uniquely responsible for its formation. In this regard, adenosine is unlike various endocrine hormones. Nor is there any evidence for storage and release of adenosine from nerve or other cells. Thus, adenosine is unlike various neurotransmitter substances.

Adenosine might be compared as a physiological regulator to the prostaglandins. In both cases the enzymes involved in the metabolic formation are ubiquitous and appear to be responsive to alterations in the physiological state of the cell. Receptors for adenosine, like those for prostaglandins, are proving to be very widespread. Finally, both prostaglandins and adenosine appear to be involved with the regulation of functions involving calcium ions. Prostaglandins, of course, derive from membrane precursors, cursors, while adenosine derives from cytosolic precursors.

Although adenosine can affect a variety of physiological functions, particular attention has been directed over the years toward actions which might lead to clinical applications. Preeminent has been the cardiovascular effects of adenosine which lead to vasodilation and hypotension but which also lead to cardiac depression. The antilipolytic, antithrombotic, and antispasmodic actions of adenosine have also received some attention. Adenosine stimulates steroidogenesis in adrenal cells, again probably via activation of adenylate cyclase. Adenosine has inhibitory effects on neurotransmission and on spontaneous activity of central neurons. Finally, the bronchoconstrictor action of adenosine and its antagonism by xanthines represents an important area of research.

It has now been recognized that there are not one but at least two classes of extracellular receptors involved in the action of adenosine. One of these has a high affinity for adenosine and, at least in some cells, couples to adenylate cyclase in an inhibitory manner. These have been termed by some as the A-1 receptors. The other class of receptors has a lower affinity for adenosine and in many cell types couples to adenylate cyclase in a stimulatory manner. These have been termed the A-2 receptors.

Characterization of the adenosine receptors has now been possible with a variety of structural analogues. Adenosine analogues resistant to metabolism or uptake mechanisms have become available. These are particularly valuable, since their apparent potencies will be less affected by metabolic removal from the effector system. The adenosine analogues exhibit differing rank orders of potencies at A-1 and A-2 adenosine receptors, providing a simple method of categorizing a physiological response with respect to the nature of the adenosine receptor. The blockade of adenosine receptors (antagonism) provides another method of categorizing a response with respect to the involvement of adenosine receptors. It should be noted that the development of antagonists specific to A-1 or A-2 adenosine receptors would represent a major breakthrough in this research field and in the preparation of adenosine receptor selective pharmacological agents having specific physiological effects in animals.

SUMMARY OF THE INVENTION

The present invention relates to compounds having the following general formula:

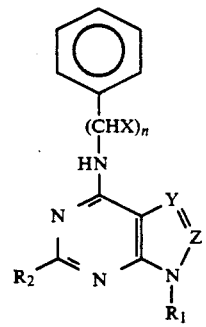

FORMULA I wherein $R_1$ is hydrogen, phenyl or $\beta$-D-ribofuranosyl; $R_2$ is hydrogen, lower alkyl of from 1 to 4 carbon atoms or lower alkoxy of from 1 to 4 carbon atoms; Y is —N= or —CH=; Z is —N= or —CH=, with the proviso that Y and Z are not identical; each X is independently hydrogen, hydroxy, lower alkyl of from 1 to 3 carbon atoms or hydroxyalkyl of from 1 to 3 carbon atoms; and n is an integer from 1 to 3.

DETAILED DESCRIPTION OF THE INVENTION

The lower alkyl groups, as indicated above, contain 1 to 4 carbon atoms and this same definition applies to any use of the term below. Similarly, the lower alkoxy groups, as indicated above, contain 1 to 4 carbon atoms and this definition applies to any use of the terms below. Examples of such alkoxy groups are methoxy, ethoxy, propoxy and butoxy.

Stereoisomerism is possible with the present compounds and the chemical structure as presented above is considered as encompassing all of the possible stereoisomers and racemic mixtures of such stereoisomers. More specifically, when X in any of the —(CHX)$_n$— as shown in Formula I is other than hydrogen, chirality is exhibited about the respective carbon atom and optical isomerism is possible.

As examples of compounds of the present invention are the following: 1. (R)-β-[(9-phenyl-9H-purin-6-yl)amino]benzenepropanol 2. (S)-β-[(9-phenyl-9H-purin-6-yl)amino]benzenepropanol 3. (S)-β-[(2-propoxy-1H-purin-6-yl)amino]benzenepropanol 4. β-[(1H-purin-6-yl)amino]benzenepropanol 5. [S-(R*,S*)]-α-[1-[(1-phenyl-6-propoxy-1H-pyrazolo[3,4-d]pyrimidin-4 yl)amino]ethyl]benzenemethanol 6. [R-(S*,R*)]-α-[1-[(1-phenyl-6-propoxy-1H-pyrazolo[3,4-d]pyrimidin-4 yl)amino]ethyl]benzenemethanol 7. β-[(1-phenyl-1H-pyrazolo[3,4-d]pyrimidin-4-yl)-amino]benzenepropanol 8. (R)-N-(1-methyl-2-phenylethyl)-1-phenyl-6-propoxy-1H-pyrazolo[3,4-d]pyrimidin-4-amine 9. (S)-N-(1-methyl-2-phenylethyl)-1-phenyl-6-propoxy-1H-pyrazolo[3,4-d]pyrimidin-4-amine 10. (S)-β-[(1-phenyl-6-propoxy-1H-pyrazolo[3,4-d]-pyrimidin-4-yl)amino]-benzenepropanol 11. (R)-β-[(1-phenyl-6-propoxy-1H-pyrazolo[3,4-d]-pyrimidin-4-yl)amino]benzenepropanol 12. (R)-β-[(2-propoxy-9-β-D-ribofuranosyl-9H-purin-6-yl)amino]benzenepropanol 13. (S)-β-[(2-propoxy-9-β-D-ribofuranosyl-9H-purin-6-yl)amino]benzenepropanol 14. (R)-N-(1-phenylpropyl)-adenosine 15. (S)-N-(1-phenylpropyl)-adenosine.

In general, the compounds of the present invention are formed by reacting, under appropriate conditions, a compound of the general structure:

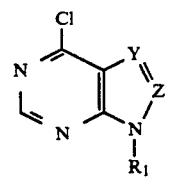

wherein Cl is chlorine: R₁ is hydrogen, phenyl or β-D-ribofuranosyl; Y is —N= or —CH=; and Z is —N= or —CH=, with the proviso that Y and Z cannot be identical, with a compound of the structure:

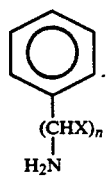

wherein each X is independently hydrogen, hydroxy or lower hydroxyalkyl of from 1 to 3, to form a compound of the structure:

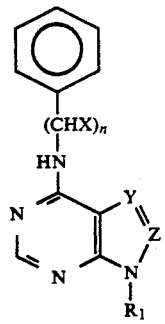

wherein R₁ is hydrogen, phenyl or β-D-ribofuranosyl; Y is —N= or —CH=; Z is —N= or —CH=, with the proviso that Y and Z cannot be identical; X is hydrogen, hydroxy or a lower hydroxyalkyl of from 1 to 3 carbon atoms and n is an integer from 1 to 3.

Likewise, compounds of the following general structure:

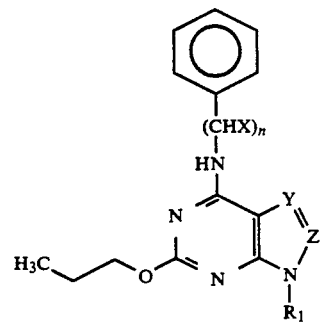

can be made by reacting a compound of the following general structure:

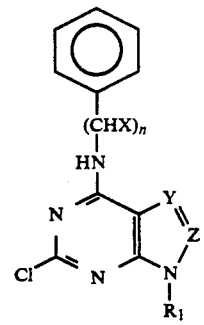

with a selected alcohol of from 1 to 4 carbon atoms, such as n-propanol.

Therapeutic Utility of Selective Adenosine Receptor Agents

The table below shows in more detail the potential therapeutic utility of selective adenosine receptor agents in accordance with the present invention:

| Area | Effect | Receptor Correlate |
|---|---|---|
| Cardiovascular | cardiotonic | A-1 antagonism |
| Cardiovascular | control tachycardia | A-1 agonism |

| Area | Effect | Receptor Correlate |
|---|---|---|
| Cardiovascular | increase coronary blood flow | A-2 agonism |
| Cardiovascular | vasodilation | A-2 (atypical) agonism |
| Pulmonary | bronchodilation | A-1 antagonism |
| Pulmonary | mediation of autocoid release from mast cells, basophils | novel adenosine receptor interaction on cell surface |
| Pulmonary | stimulate respiration; treat paradoxical ventilatory response (infants) | Ado antagonism |
| Renal | inhibit renin release | A-1 agonism |
| Central Nervous System | aid in opiate withdrawal | Ado agonism |
| Central Nervous System | analgesic | A-1 agonism |
| Central Nervous System | anticonvulsant | A-1 agonism |
| Central Nervous System | antidepressant | A-1 agonism |
| Central Nervous System | antipsychotic | Ado agonism |
| Central Nervous System | anxiolytic | agonism |
| Central Nervous System | inhibition of self-mutilation behavior (Lesch-Nyhan syndrome) | Ado agonism |
| Central Nervous System | sedative | A-2 agonism |

In the cardiovascular, pulmonary and renal system targets, designed compounds which are identified by receptor binding studies can be evaluated in functional *in vivo* tests which are directly indicative of the human physiological response. A good description of the pharmacology and functional significance of purine receptors is presented by M. Williams in *Ann. Rev. Pharmacol. Toxicol.*, 27, 31 (1987). In a section entitled "Therapeutic Targeting of Adenosine Receptor Modulators" it is stated that "adenosine agonists may be effective as antihypertensive agents, in the treatment of opiate withdrawal, as modulators of immune competence and renin release, as antipsychotics and as hypnotics. Conversely, antagonists may be useful as central stimulants, inotropics, cardiotonics, antistress agents, anti-asthmatics, and in the treatment of respiratory disorders." The smorgasbord of activities displayed by adenosine receptor agents underscores their great potential utility for therapy and the need for central agents.

Adenosine exerts its various biological effects via action on cell-surface receptors. These adenosine receptors are of two types: A-1 and A-2. The A-1 receptors are operationally defined as those receptors at which several N6-substituted adenosine analogs such as R-phenylisopropyladenosine (R-PIA) and cycloadenosine (CHA) are more potent than 2-chloroadenosine and N-5'-ethylcarboxamidoadenosine (NECA). At A-2 receptors the order of potency is instead NECA>2-chloroadenosine>R-PIA>CHA.

As illustrated in the table above, adenosine receptors govern a variety of physiological functions. The two major classes of adenosine receptors have already been defined. These are the A-1 adenosine receptor, which is inhibitory of adenylate cyclase, and the A-2 adenosine receptor, which is stimulatory to adenylate cyclase. The A-1 receptor has a higher affinity for adenosine and adenosine analogs than the A-2 receptor. The physiological effects of adenosine and adenosine analogs are complicated by the fact that non-selective adenosine receptor agents first bind the rather ubiquitous low-affinity A-2 receptors, then as the dose is increased, the high-affinity A-2 receptors are bound, and finally, at much higher doses, the very high-affinity A-1 adenosine receptors are bound. (See J.W. Daly, et al., Subclasses of Adenosine Receptors in the Central Nervous System: Interaction with Caffeine and Related Methylxanthines, *Cellular and Molecular Neurobiology*, 3,(1), 69-80 (1983).)

In general, the physiological effects of adenosine are mediated by either the stimulation or the inhibition of adenylate cyclase. Activation of adenylate cyclase increases the intracellular concentration of cyclic AMP, which, in general, is recognized as an intracellular second messenger. The effects of adenosine analogs can therefore be measured by either the ability to increase or the ability to antagonize the increase in the cyclic AMP in cultured cell lines. Two important cell lines in this regard are VA 13 (WI-38 VA 13 2RA), SV-40 transformed WI 38 human fetal lung fibroblasts, which are known to carry the A-2 subtype of adenosine receptor, and fat cells, which are known to carry the A-1 subtype of adenosine receptor. (See R.F. Bruns, Adenosine Antagonism by Purines, Pteridines and Benzopteridines in Human Fibroblasts, *Chemical Pharmacology*, 30, 325-33 (1981).)

It is well known from *in vitro* studies that the carboxylic acid congener of 8-phenyl-1,3-dipropyl-xanthine (XCC) is adenosine receptor nonselective, with a Ki at the A-1 receptors in brain membranes of 58±3nM and a Ki at the A-2 receptors of the brain slice assay of 34±13nM. The amino congener of 8-phenyl-1,3-dipropyl-xanthine (XAC), on the other hand, has a 40-fold higher affinity for A-1 adenosine receptors, with a Ki of 1.2±0.5nM, as compared with a Ki at the A-2 receptors of the brain slice assay of 49±17nM. In addition, XAC is much more potent in antagonizing the effects of adenosine analogs on heart rate than on blood pressure. Since it is generally known that the adenosine analog-induced effects on the heart seem to be mediated via A-1 receptors and those on blood pressure via A-2 receptors, the selectivity of XAC under *in vivo* conditions suggests that adenosine receptor activity *in vitro* correlates with adenosine receptor activity *in vivo* and that specific physiological effects can be distinguished as a result of this selectivity. (See B.B. Fredholm, K.A. Jacobsen, B. Jonzon, K.L. Kirk, Y.O. Li, and J.W. Daly, Evidence That a Novel 8-Phenyl-Substituted Xanthine Derivative is a Cardioselective Adenosine Receptor Antagonist In Vivo, *Journal of Cardiovascular Pharmacology*, 9, 396-400 (1987), and also K.A. Jacobsen, K.L. Kirk, J.W. Daly, B. Jonzon, Y.O. Li, and B.B. Fredholm, Novel 8-Phenyl-Substituted Xanthine Derivative Is Selective Antagonist At Adenosine Receptors In Vivo, *Acta Physiol. Scand.*, 341-42 (1985).)

It is also known that adenosine produces a marked decrease in blood pressure. This blood pressure reduction is probably dependent upon an A-2 receptor-mediated decrease in peripheral resistance. Adenosine analogs are also able to decrease heart rate. This effect is probably mediated via adenosine receptors of the A-1 subtype.

Thus, it is readily apparent that the pharmacological administration of the adenosine receptor selective adenosine analogs disclosed herein will result in selective binding to either the A-2 or the A-1 receptor, which will, in turn, selectively result in either a decrease in blood pressure or a decrease in heart rate, for example, thereby decoupling these physiological effects *in vivo*. The selection of such adenosine receptor selective agents can be determined by the methods described in further detail below.

Test For Affinity For Brain Adenosine A-2 Receptors

The test described below was used to determine the potency of test compounds to compete with the ligand [3H]-5'-N-ethyl-carboxamidoadenosine (NECA) for the adenosine A-2 receptors prepared from animal brain membranes. (See also R.R. Bruns, G.H. Lu, and T.A. Pugsley, Characterization of the A-2 Adenosine Receptor Labeled by [3H]NECA in Rat Striatal Membranes, *Mol. Pharmacol.*, 29, 331-346 (1986).) Young male rats (C-D strain), obtained from Charles River, are killed by decapitation and the brains are removed. Membranes for ligand binding are isolated from rat brain striatum. The tissue is homogenized in 20 vol ice-cold 50 mM Tris-HCl buffer (pH 7.7) using a polytron (setting for 6 to 20 seconds). The homogenate is centrifuged at 50,000 $\times$g for 10 minutes at 4° C. The pellet is again homogenized in a polytron in 20 vol of buffer, and centrifuged as before. The pellet is finally resuspended in 40 vol of 50mM Tris-HCl (pH 7.7) per gram of original wet weight of tissue.

Incubation tubes, in triplicate, receive 100 $\mu$l of [3H]NECA (94 nM in the assay), 100 $\mu$l l of 1 $\mu$M cyclohexyladenosine (CHA), 100 $\mu$l of 100 mM MgCl$_2$, 100 $\mu$l of 1 IU/ml adenosine deaminase, 100 $\mu$l of test compounds at various concentrations over the range of $10^{10-10}$ M to $10^4$ M diluted with assay buffer (50 mM Tris-HCl, pH 7.7) and 0.2 $\mu$l of membrane suspension (5 mg wet weight), in a final volume of 1 ml of 50 mM Tris-HCl, pH 7.7. Incubations are carried out at 25° C. for 60 minutes. Each tube is filtered through GF/B glass fiber filters using a vacuum. The filters are rinsed two times with 5 ml of the ice-cold buffer. The membranes on the filters are transferred to scintillation vials to which 8 ml of Omnifluor with 5% Protosol is added. The filters are counted by liquid scintillation spectrometry.

Specific binding of [3H]NECA is measured as the excess over blanks run in the presence of 100 $\mu$M 2-chloroadenosine. Total membrane-bound radioactivity is about 2.5% of that added to the test tubes. Since this condition limits total binding to less than 10% of the radioactivity, the concentration of free ligand does not change appreciably during the binding assay. Specific binding to membranes is about 50% of the total bound. Protein content of the membrane suspension is determined by the method of O.H. Lowry, N.J. Rosebrough, A.L. Farr and R.J. Randall, Protein Measurements With Folin Phenol Reagent, *J. Biol. Chem.*, 193, 265-275 (1951). .

Displacement of [3H]NECA binding of 15% or more by a test compound is indicative of affinity for the adenosine A-2 site. The molar concentration of a compound which causes 50% inhibition of the binding of ligand is the IC$_{50}$. A value in the range of 100-1000 nM would indicate a highly potent compound.

Test For Affinity For Brain Adenosine A-1 Receptor Binding Sites

The test described below is used to determine the potency of test compounds to compete with the ligand [3H]-cycloadenosine for the Adenosine A-1 receptor prepared from rat brain membranes. Male Sprague-Dawley rats are sacrificed by decapitation and the membranes are isolated from whole animal brains. (See R. Goodman, M. Cooper, M. Gavish, and S. Synder, Guanine Nucleotide and Cation Regulation of the Binding of [3H]Diethylphenylxanthine to Adenosine A-1 Receptors in Brain Membrane, *Molecular Pharmacology*, 21, 329-335 (1982).)

Membranes are homogenized (using polytron setting 7 for 10 seconds) in 25 volumes of ice-cold 50 mM Tris-HCl buffer, pH 7.7. The homogenate is centrifuged at 19,000 rpm for 10 minutes at 4° C. The pellet is washed by resuspending in 25 volumes of buffer with 2 IU of adenosine deaminase per ml and incubated 30 minutes at 37° C. The homogenate is centrifuged again. The final pellet is resuspended in 25 volumes of ice-cold buffer.

The incubation tubes, in triplicate, receive 100 $\mu$l of [3H]cyclohexyladenosine, 0.8 nM in the assay, 200 $\mu$l of test compounds at various concentrations over the range of $10^{-10}$ M to $10^{-6}$ M diluted with 50 nM Tris-HCl buffer (pH 7.7), 0.2 ml of membrane suspension (8 mg wet weight) and in a final volume of 2 ml with Tris buffer. Incubations are carried out at 25° C. for 2 hours and each one is terminated within 10 seconds by filtration through a GF/B glass fiber filter using a vacuum. The membranes on the filters are transferred to scintillation vials. The filters are counted by liquid scintillation spectrometry in 8 ml of Omniflour containing 5% Protosol.

Specific binding of [3H]cycloadenosine is measured as the excess over blanks taken in the presence of $10^5$ M 2-chloroadenosine. Total membrane-bound radioactivity is about 5% of that added to the test tubes. Specific binding to membranes is about 90% of the total bound. Protein content of the membrane suspension is determined by the method of Lowry, et al. Ibid., 265.

Displacement of [3H]cyclohexyladenosine binding of 15% or more by a test compound is indicative of affinity for the adenosine binding site.

Obtained Usinq The Above Described Test Procedures

The following is a table showing the adenosine receptor binding affinities for several compounds (refer to compound examples on page 5 for cross reference to compound names) within the scope of the present invention:

| Compound | A-1 Receptor Ki | A-2 Receptor Ki | A-2 Ki/A-1 Ki |
|---|---|---|---|
| 1. | $7.40 \times 10^{-6}$ | $6.38 \times 10^{-5}$ | 11.80 |
| 2. | $4.80 \times 10^{-6}$ | $4.54 \times 10^{-5}$ | 13.00 |
| 3. | $1.10 \times 10^{-7}$ | $5.90 \times 10^{-6}$ | 72.20 |
| 4. | $2.90 \times 10^{-5}$ | $>1.99 \times 10^{-4}$ | — |
| 5. | $5.53 \times 10^{-6}$ | $4.06 \times 10^{-6}$ | 0.73 |
| 6. | $6.43 \times 10^{-7}$ | $1.31 \times 10^{-6}$ | 2.04 |
| 7. | $1.80 \times 10^{-6}$ | $1.60 \times 10^{-6}$ | 0.89 |
| 8. | $2.01 \times 10^{-6}$ | $3.63 \times 10^{-6}$ | 1.80 |
| 9. | $1.13 \times 10^{-5}$ | $>6.99 \times 10^{-}$ | — |
| 10. | $1.74 \times 10^{-6}$ | $2.90 \times 10^{-6}$ | 1.67 |
| 11. | $3.21 \times 10^{-7}$ | $3.77 \times 10^{-7}$ | 1.17 |
| 12. | $3.70 \times 10^{-6}$ | $1.72 \times 10^{-5}$ | 4.65 |
| 13. | $4.40 \times 10^{-8}$ | $1.90 \times 10^{-6}$ | 43.18 |
| 14. | $6.5 \times 10^{-9}$ | $0.85 \times 10^{-6}$ | 131.00 |
| 15. | $0.66 \times 10^{-6}$ | $14.4 \times 10^{-6}$ | 22.00 |

The nucleotide guanosine triphosphate (GTP) has been shown to differentially affect the binding of agonists and antagonists to a variety of neurotransmitter receptors. In general, guanine nucleotides lower the affinity of agonists for receptors without a concomitant decrease in antagonist affinity. Accordingly, GTP has been shown to decrease the potency of agonists but not antagonists as inhibitors of the binding of the adenosine antagonist [3H]3-diethyl-8-phenylxanthine. In general, GTP greatly reduces the potency of purine agonists, but not antagonists as inhibitors of [3H]phenylisopropyl adenosine binding and is, therefore, an effective agent for distinguishing between agonists and antagonists. (See L.P. Davies, S.C. Chow, J.H. Skerritt, D.J. Brown and G.A.R. Johnston, Pyrazolo [3,4-d]- Pyrimidines as Adenosine Antagonists, *Life Sciences*, 34, 2116–27 (1984).) It is understood, in general, that adenosine analogs act as agonists if β-D-ribofuranosyl is present in the molecule at the $R_1$ position and as an antagonist if $R_1$ is hydrogen or phenyl.

Pharmaceutical Preparations of the Adenosine Receptor Selection Adenosine Analogs The exact amount of the compound or compounds to be employed, i.e., the amount of the subject compound or compounds sufficient to provide the desired effect, depends on various factors such as the compound employed; type of administration; the size, age and species of animal; the route, time and frequency of administration; and, the physiological effect desired. In particular cases, the amount to be administered can be ascertained by conventional range finding techniques.

The compounds are preferably administered in the form of a composition comprising the compound in admixture with a pharmaceutically acceptable carrier, i.e., a carrier which is chemically inert to the active compound and which has no detrimental side effects or toxicity under the conditions of use. Such compositions can contain from about 0.1 μg or less to 500 mg of the active compound per ml of carrier to about 99% by weight of the active compound in combination with a pharmaceutically-acceptable carrier.

The compositions can be in solid forms, such as tablets, capsules, granulations, feed mixes, feed supplements and concentrates, powders, granules or the like; as well as liquid forms such as sterile injectable suspensions, orally administered suspensions or solutions. The pharmaceutically acceptable carriers can include excipients such as surface active dispersing agents, suspending agents, tableting binders, lubricants, flavors and colorants. Suitable excipients are disclosed, for example, in texts such as *Remington's Pharmaceutical Manufacturing*, 13 Ed., Mack Publishing Co., Easton, Pennsylvania (1965).

The following examples are presented to illustrate the present invention but they should not be construed as limiting in any way.

EXAMPLE 1

To a solution of 2.5 g of 2,6-dichloropurine dissolved in 50 ml ethanol was added 2.0 g (S)-(-)-2-amino-3-phenyl 1-propanol, and 1.83 ml Et3N with stirring at room temperature for 2 hours. The mixture was then heated to reflux for 20 hours. The solvent was removed under vacuum and the residue purified by flash chromatography (5–10% MeOH/CHCl3) to yield 3.68 g of a yellow solid, S-8-[(2-chloro-1H-purin-6-yl)amino]benzenepropanol (m.p. 117°-123° C.).

This was followed by suspension of 1.42 g of the above product in 30 ml CHCl3 and treatment with 1.30 g triphenylmethylchloride and 0.65 ml Et3N. After 3 hours the reaction was diluted with 200 ml CHCl3 and remixed with 200 ml saturated NaHCO3, 200 ml saturated NaCl, dried over MgSO4, filtered and concentrated to yield 3.3 g of a yellow solid. This was flash chromatographed (5% MeOH/CHCl3) to yield 2.16 g of a foam product, S-62 -[(9-triphenylmethyl-2-chloro-1H-purin-6-yl)amino]benzenepropanol.

To a solution of 330 mg sodium dissolved in 100 ml n-propanol was added 2.15 g of S-8-[(9-triphenylmethyl-2-chloro-1H-purin-6-yl)amino]benzenepropanol and the reaction was heated to reflux for 6 hours. It was then cooled to room temperature, poured into 300 ml H2O and extracted with CHCl3 (3 times 200 ml). The combined organic extracts were washed with 300 ml saturated NaCl, dried over Na2SO4, filtered and concentrated to yield 2.16 g of a foam product, S-β-[(2-propoxy-9-triphenylmethyl-1H-purin-6-yl)amino]-benzenepropanol.

Subsequently, 2.14 g of S-β-[(2-propoxy-9-triphenylmethyl-1H-purin-6yl)amino]benzenepropanol was dissolved in 50 ml CH2Cl2 followed by addition of p-toluenesulfonic acid (0.71g). After stirring 24 hours the solvent was removed under vacuum and the residue was purified by flash chromatography (5–10% MeOH/CHCl 3) to yield 0.81 g of a white solid, (S)-β-[(2-propoxy-1H-purin-6-yl)amino]benzenepropanol (m.p. 229°–231° C.).

EXAMPLE 2

2.0 g of 6-chloro-9-phenylpurine was combined with 1.38 g R-(+)-2-amino-3-phenyl-1-propanol, 1.27 ml Et3N, 50 ml absolute ethanol and heated to reflux for 5 hours. The solvent was then removed and the residue was purified by flash chromatography (5% MeOH/CHCl3), followed by a second purification (2.5-5% MeOH/CHCl3) to yield 2.66 g of a white foam (88% yield). This was recrystallized from 10% isopropyl alcohol/hexane and dried under vacuum at 90° C. for four days to yield 1.28 g of a white solid, (R)-β-[(9-phenyl-9H-purin-6-yl)amino]benzenepropanol (m.p. 130°–132° C.).

EXAMPLE 3

2.0 g of 6-chloro-9-phenylpurine was combined with 1.38g S-(-)-2-amino-3-phenyl-1-propanol, 1.27 ml Et3N, 50 ml ethanol and heated to reflux for 5 hours. The solvent was then removed under vacuum and the residue purified by flash chromatography (2.5-5% MeOH/CHCl3) to yield 2.27 g of product (76% yield). This was then recrystallized from isopropyl alcohol/hexane 10% to yield after drying under vacuum at 90° C. for 3 days 0.87 g of a white solid, (S)-β-(9-phenyl-9H-purin-6-yl)amino]benzenepropanol (m.p. 130°–132° C.).

EXAMPLE 4

1.94 g of D-amphetamine sulfate was made basic with 10% KOH. The aqueous solution was extracted with ether. The organic layer was dried over MgSO4, filtered, and concentrated to yield a clear oil. This was diluted with 3 ml of ethanol and added to a stirred solution of 466 g of 1-phenyl-4,6-dichloropyrazolo[3,4-d]pyrimidine in 7 ml ethanol. After 48 hours the solvent was removed under vacuum and the crude material was purified by radial chromatography (20–40% ethyl alcohol/hexane, 2mm plate) to yield 640 mg of (S)-N-(1-methyl-2-phenylethyl)-1-phenyl-6-chloro-1H-pyrazolo[3,4-d]pyrimidin-4-amine (100%).

Next, 324 mg sodium was reacted with 10 ml of n-propanol. To this, 640 mg of (S)-N-(1-methyl-2-phenylethyl)-1-phenyl-6-chloro-6-chloro-1H-pyrazolo[3,4-d]pyrimidin-4-amine in 5 ml of d-propanol was added with stirring and the reaction was heated to 90° C. for 2 hours. It was then cooled, diluted with 200 ml saturated NaCl, and extracted with 200 ml CHCl3. The organic layer was dried over MgSO4, filtered, and concentrated to yield an oil which was purified by radial chromatography (30-50% Et2O/hexane) to yield after recrystalliza+tion from 30% Et2O/hexane 382 mg of product (m.p. 134°-136° C.). Proton NMR indicated ether was still present. The compound was then oven dried under vacuum for 6 hours to yield 318 mg of (S)-N-(1-methyl-2-phenylethyl)-1-phenyl-6-propoxy-1H-pyrazolo[3,4-d]pyrimidin-4-amine (m.p. 134°-136° C.).

EXAMPLE 5

1.94 g of L-amphetamine sulfate was dissolved in H2O, made basic, and extracted with ether. The ether layer was concentrated under vacuum, the oil was taken up in 3 ml ethanol, and added to a stirred suspension of 465 mg 1-phenyl-4,6-dichloropyrazolo[3,4-d]pyrimidine in 7 ml ethanol. After 24 hours the solvent was removed under vacuum and the crude oil was purified by radial chromatography (40-60% Et2O/hexane, 2 mm plate) to yield 531 mg of (R)-N-(1-methyl-2-phenylethyl)-1-phenyl-6-chloro-1H-pyrazolo[3,4-d]pyrimidin-4pyrazolo[3,4-d]pyrimidin-4-amine (83%).

Next, 268 mg sodium was reacted with 10 ml of n-propanol. 531 mg of (R)-N-(1-methyl-2-phenylethyl)-1-phenyl-6-chloro-1H-pyrazolo[3,4-d]pyrimidin-4-amine in 5 ml n-propanol was added to the stirred solution under nitrogen. The reaction was heated (oil bath 90° C.) for 2 hours. It was then cooled, diluted with 100 ml saturated NaCl, and the aqueous solution was extracted with 200 ml CHCl3. The organic layer was then dried over MgSO4,filtered, and concentrated to yield an oil which was purified by radial chromatography (30-50% Et2O/hexane, 2mm plate) to yield, after recrystallization from 30% Et2O/hexane, 381.4 mg of a white solid (m.p. 135°-137° C.). Proton NMR indicated ether was still present. Thus the compound was oven dried under vacuum (setting at 3) for 6 hours to yield 326 mg of final product, (R)-N-(1-methyl-2-phenylethyl)-1-phenyl-6-propoxy 1H-pyrazolo[3,4d]pyrimidin-4-amine (m.p. 135°-137° C.).

EXAMPLE 6

1 g of 1-phenyl-4,6-dichlorpyrazolo[3,4d]pyrimidine was suspended in 25 ml ethanol. 1.71 g of 1R,2S-norephedrine was added with stirring. After 24 hours the solvent was removed under vacuum and the crude oil was purified by radial chromatography (40-50-60-70% Et2O/hexane, 4mm plate) to yield 1.17 g of a white solid, [S-(R*,S*)]-β-[1-[(1-phenyl-6-chloro-1H-pyrazolo[3,4-d]pyrimidin-4-yl)-amino]ethyl]benzenemethanol (m.p. 164°-165° C., 82% yield).

Next, 194 mg sodium was reacted with 10 ml of n-propanol. 400 mg of [S-(R*,S*)]-β-[1-[(1-phenyl-6-chloro-11H-pyrazolo[3,4-d]pyrimidin-4-yl)amino]ethyl]benzenemethanol in 5 ml of n-propanol was added to the stirred solution under nitrogen. The reaction was heated to 90° C. for 2 hours. It was then diluted with 100 ml saturated NaCl, extracted with 200 ml CHCl3, filtered, and concentrated under vacuum to yield an oil which was purified by radial chromatography (5-10-20% isopropyl alcohol/hexane, 4 mm plate) to yield 423 mg of an oil. Recrystallization from 20% Et2O/hexane and vacuum oven drying at 70° C. for 24 hours yield 122 mg of [S-(R*,S*)]-β-[1-[(1-phenyl-6-propoxy-1H-pyrazolo[3,4-d]pyrazolo[3,4-dpyrimidin-4-yl)amino]ethyl]benzenemethanol (m.p. 136°-136° C.).

EXAMPLE 7

390 mg of 1-phenyl-4,6-dichloropyrazolo[3,4-d]pyrimidine was suspended in 15 ml 95% ethanol. 828 mg norephedrine HCl was dissolved in 100 ml H2O, made basic with 10% KOH, and the free base extracted with 100 ml ether. The organic was dried over MgSO4, filtered, and concentrated to yield an oil which was added to the stirred reaction. After 4 hours the solution became clear and the solvent was removed under vacuum. The crude oil was then purified by radial chromatography (5-10-20% isopropyl alcohol/hexane, 4mm plate) to yield 535 mg of [R-(S*,R*)]-β-]1-[(1-phenyl-6-chloro-1H-pyrazolo[3,4-d]pyrimidin-4-yl)-amino]ethyl]benzenemethanol (90%).

Next, 165 mg sodium was reacted with 10 ml of n-propanol. 341 mg of [R-(S*,R*)]-β-]1-[(1-phenyl-6-chloro-1H -pyrazolo[3,4-d]pyrimidin-4-yl)-amino]ethyl]benzenemethanol pyrimidin-4-yl)amino]ethyl]benzenemethanol in 3 ml of n-propanol was added with stirring and heated to 90° C. under nitrogen. After 2 hours the reaction was cooled and poured into 100 ml saturated NaCl. It was then extracted with 200 ml CHCl3, dried over MgSO4, filtered, and concentrated to yield an oil which was purified by radial chromatography (5-10-20% isopropyl alcohol/hexane, 2 mm plate) to yield 326 mg product. This was recrystallized from 20% Et2O/hexane to yield 205 mg of a white solid, [R-(S*,R*)]β[1-[(1-phenyl-6-propoxy-1H-pyrazolo[3,4-d]-pyrimidin-4-yl)amino]ethyl]benzenemethanol (m.p. 137°-140° C.).

EXAMPLE 8

First, 2.5 g of 1-phenyl-4,6-dichloropyrazolo[3,4-d]-pyrimidine was suspended in 60 ml ethanol, then 4.28 g (S)-(-)-2 amino-3-phenyl-1-propanol was added and the reaction was allowed to stir for 24 hours. The solvent was then removed under vacuum and the crude oil was purified by flash chromatography (10-15-20% isopropyl alcohol/hexane) to yield 3.5 g of product (S)-8-[(1-phenyl-6-chloro-1H-pyrazolo[3,4-d]pyrimidin-4-yl)amino]-benzenepropanol (97%).

Next, 314 mg sodium was reacted with 15 ml of n-propanol. 650 mg of (S)-β-[(1-phenyl-6-chloro-1H-pyrazolo-[3,4-d]pyrimidin-4-yl)amino]benzenepropanol dissolved in 10 ml of n-propanol was added to the reaction with stirring under nitrogen. The reaction was then heated to 90° C. for two hours. After cooling it was poured into 100 ml saturated NaCl and extracted with 200 ml CHCl3. The organic layer was dried over MgSO4, filtered, and concentrated to yield an oil which was purified by radial chromatography (10-20% isopropyl alcohol/hexane) to yield after recrystallization from 30% isopropyl alcohol/hexane and oven drying under vacuum at 60° C. for 72 hours, 319 mg of (S)-β-[(1-phenyl-6-propoxy-1H-pyrazolo[3,4-d]pyrimidin-4-yl)amino]benzenepropanol (46%, m.p. 155-157° C.).

EXAMPLE 9

First, 2.81 g of 1-phenyl-4,6-dichloropyrazolo[3,4-d]pyrimidine was suspended in 60 ml of ethanol, then 3.2 g of (R)-(+)-2-amino-3-phenyl-1-propanol was added with stirring. After 48 hours the solvent was removed under vacuum and the oil was flash chromatographed (2-5-7% MeOH/CHCl₃) to yield 3.80 g of (R)-β-[(1-phenyl-6-chloro-1H-pyrazolo[3,4-d]pyrimidin-4-yl)amino]benzenepropanol (95%).

Next, 380 mg of sodium was reacted with 10 ml of n-propanol. 773 mg of (R)-β-[(1-phenyl-6-chloro-1H-pyrazolo -[3,4-d]pyrimidin-4-yl)amino]benzenepropanol in 5 ml of n-propanol was added with stirring. The reaction was heated to 90° C. in an oil bath for 2.5 hours, then the solvent was removed under vacuum, the residue taken up in 200 ml CHCl₃. The organic layer was washed with saturated NaCl, dried over MgSO₄, filtered, and concentrated to an oil which was purified by radial chromatography (10-20-30% isopropyl alcohol/hexane, 4 mm plate) to yield after recrystallization from 30% isopropyl alcohol/hexane 217 mg of a white solid (m.p. 158°-159° C.). Proton NMR indicated n-propanol was still present, so this product was oven dried under vacuum (setting at 3) to yield 161 mg of final product, (R)-8-[(1-phenyl-6-propoxy-1H-pyrazolo[3,4-d]pyrimidin-4-yl)-amino]benzenepropanol (m.p. 157°-158° C.).

EXAMPLE 10

First, 5 g of 2,6-dichloropurine and 8.4 g of ribose tetraacetate were combined and heated to 155° C. with stirring to produce a heterogenous suspension. A drop of concentrated H₂SO₄ was added and the reaction was allowed to stir at 155° C. until it became clear. The reaction was cooled and the HOAc was removed under vacuum. 30 ml of ethanol was added and trituration, followed by filtration, yielded 3.7 g of product. This was recrystallized from 175 ml ethanol to yield 2.31 g of 2,6-dichloro-9-(2,3,5-tri-O -acetyl-β-D-ribofuranosyl)-9H-purine with melting point of 154°-156° C. as long flat needles.

2.0 g of 2,6-dichloro-9-(2,3,5-tri-O -acetyl-β-D-ribofuranosyl)-9H-purine was combined with 0.67 g of S-(-)-2-amino-3-phenyl-1-propanol, 0.67 ml triethylamine, and heated to reflux for 16 hours. The solvent was removed and the residue was purified by flash chromatography (5-10% methanol/trichloromethane) to yield 0.90 g of a foam. Less pure fractions were rechromatographed as above to provide a total of 1.81 g of (S)-β-[(9-(2,3,5-tri-O-acetyl-β-D-ribofuranosyl)-2-chloro-1H-purin-6-yl)amino]benzenepropanol.

Next, 0.59 g of sodium was reacted with 60 ml of n-propanol. The n-propoxide was then added to a stirring solution of 1.8 g of (S)-β-[(9-(2,3,5-tri-O-acetyl-β-D-ribofuranosyl)-2-chloro-1H-purin-6-yl)amino]benzenepropanol in 60 ml n-propanol and heated to reflux. After 16 hours, 3 ml water was added followed by MgSO₄. The reaction was filtered and concentrated under vacuum. The residue was purified by flash chromatography (20-30% methanol/trichloromethane) to yield 840 mg of product. This was recrystallized from about 20% isopropyl alcohol/hexane and dried under high vacuum for 7 days to yield 197 mg of (S)-β-[(2-propoxy-9-(β-D-ribofuranosyl)-1H-purin-6-yl)amino]-benzenepropanol as a white solid (m.p. 102°-104° C.).

EXAMPLE 11

First, 1.9 g of 2,6-dichloropurine and 3.2 g protected ribose (β-D-ribofuranose-1,2,3,5-tetraacetate) were combined and placed in an oil bath at 155° C. After 2 minutes of stirring a capillary drop of concentrated H₂SO₄ was added and the reaction became homogeneous. After stirring an additional 10 minutes the reaction was cooled, the HOAc was removed under high vacuum and heat, and 15 ml of absolute ethanol added. The residue was dissolved with heat and the solution was placed in a freezer at −21° C. The white preciptate was collected and recrystallized from 100 ml absolute ethanol to yield after drying under vacuum at 80° C. for 4 hours 2.16 g of 2,6-dichloro-9-(2,3,5-tri-O-acetyl-β-D-ribofuranosyl)-9H-purine having a melting point of 154°-157°C.

21 g of 2,6-dichloro-9-(2,3,5-tri-O-acetyl-β-D-ribofuranosyl)-9H-purine was combined with 0.7 g of R-(+)-2-amino-3-phenyl-1-propanol, 0.7 ml triethylamine and 75 ml absolute ethanol and heated to reflux for 4 hours. The solvent was removed under vacuum and the residue purified by flash chromatography (5-10% methanol/trichloromethane) to yield 2.27 g of (R)-β-[(9-(2,3,5-tri-O-acetyl-β-D-ribofuranosyl)-2-chloro-1H-purin-6-yl)amino]benzenepropanol.

Next, 0.72 g of sodium was reacted in 150 ml n-propanol. This solution was added to 2.2 g of (R)-β-[(9-(2,3,5-tri-O-acetyl-β-D-ribofuranosyl)-2-chloro-1H-yl)amino]benzenepropanol with stirring. The reaction was heated to reflux for 8 hours. After cooling the reaction was filtered and concentrated under vacuum. The residue was purified by flash chromatography (20-30% methanol/trichloromethane) to yield 930 mg of a foam product. This was recrystallized from about 10% isopropyl alcohol/hexane to yield after drying under vacuum at 80° C for 24 hours 590 mg of (R)-β-[(9-(2,3,5-tri-O-acetyl-β-D-ribofuranosyl)-2-chloro-1H-purin-6-yl)amino]benzenepropanol as a white solid. (m.p. 149°-152° C.

EXAMPLE 12

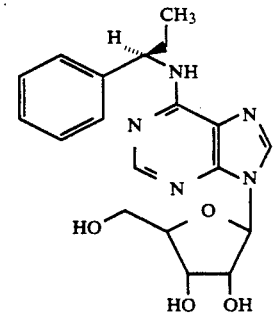

Preparation of (R)-N-(1-phenylpropyl)-adenosine

Following the general procedure described by Schrecker (J. Org. Chem., 22, 33 (1957)), prepare the primary amine by dissolving R-(-)-2-phenylbutyric acid (6.76 g, 41.2 mmol) in benzene (50 ml). Treat the solution with oxalyl chloride (7.1 ml, 82.3 mmol) and slowly heat the solution to 70° C. for 1 hour. After cooling, remove the solvent under vacuum at 38° C. Add benzene (2×50 ml) and again remove the solvent under vacuum at 38° C. Dissolve the residue in acetone (25 ml) and add sodium azide (4 g in 12 ml water, 61.8 mmol) at 0° C. rapidly with stirring. After 1 hour extract the reaction with benzene (2×150 ml). Combine the organic extracts, dry over anhydrous magnesium sulfate, and filter. Slowly heat the filtrate to approximately 62° C. for 1 hour (nitrogen evolution). Cool the reaction, remove the solvent under vacuum, and add concentrated hydrochloric acid (22 ml) with stirring. Heat the reaction to 45° C. for 15 minutes. After cooling, add water (200 ml) and rinse the aqueous with diethyl ether (500 ml). Treat the aqueous ( solution cautiously with sodium hydroxide until it becomes basic. Extract the aqueous with diethyl ether (4×150 ml), combine the organic extracts, dry over anhydrous sodium sulfate, filter, and concentrate under vacuum to provide the crude primary amine (4.53 g). Purify by flash chromatography (5 to 10% methanol/chloroform) to yield R-(+)-1-phenylpropyl amine (3.52 g, $[\alpha]_D^{20} = +15.4°$ C. (C=1.4, chloroform)).

Combine 6-chloropurine riboside (1 g, 3.49 mmol), the R-(+)-1-phenylpropyl amine (0.47 g, 3.49 mmol) prepared above, triethylamine (0.35 g, 3.49 mmol), and methanol (100 ml). Heat the reaction to reflux for 6 hours. After cooling, remove the solvent under vacuum and purify the residue by flash chromatography (5 to 10% methanol/chloroform) to provide 0.43 g of compound as a white foam. Dry over phosphorous pentoxide under high vacuum to yield the title compound (80 mg, m.p. 65°-74° C., $[\alpha]_D^{20} = -29.8°$ C. (C=1.06, chloroform)).

EXAMPLE 13

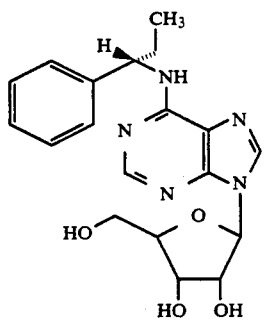

Preparation of (S)-N-(1-phenylpropyl)-adenosine

Following the general procedure described by Schrecker (Ibid), prepare the primary amine in a manner analogous to that described in Example 12 from S-(+)-2-phenylbutyric acid (6 g, 36.5 mmol) to yield S-(-)-1-phenylpropyl amine (2 75 g, $[\alpha]_D^{20} = -17.7°$ C. (C=0.976, chloroform)).

Combine 6-chloropurine riboside (1 g, 3.49 mmol), the S-(-)-1-phenylpropyl amine (0.47 g, 3.49 mmol) prepared above, triethylamine (0.35 g, 3.49 mmol), and methanol (50 ml). Heat the reaction to reflux for 7 hours. After cooling, remove the solvent under vacuum and purify the residue by flash chromatography (5 to 10% methanol/chloroform) to yield the title compound (0.72 g), m.p. 73°-84° C., [60 $]_D^{20} = -51.5°$ C. (C=1.00, chloroform).

What is claimed is:

1. A compound according to the formula:

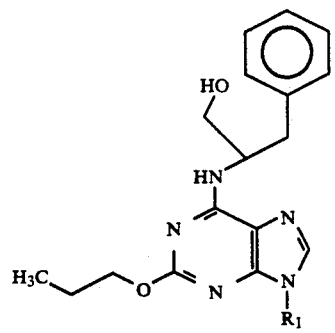

wherein $R_1$ is hydrogen, phenyl or β-D-ribofuranosyl.

2. A compound according to claim 1 which is β-[(2-propoxy-1H-purin-6-yl)amino]benzenepropanol.

3. A compound according to claim 1 which is (R)-β-[(2-propoxy-9-β-D-ribofuranosyl-9H-purin-6-yl)amino]benzenepropanol.

4. A compound according to claim 1 which is (S)-β-[(2-propoxy-9-β-D-ribofuranosyl-9H-purin-6-yl)amino]benzenepropanol.

5. A compound of the formula:

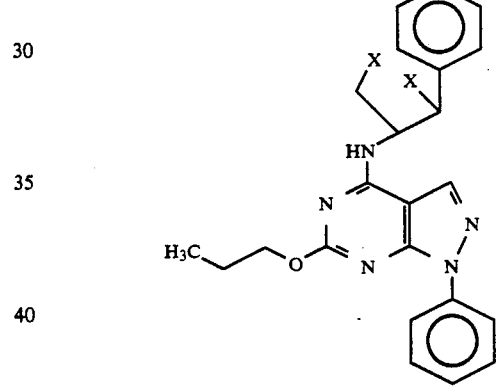

wherein each X is independently either hydrogen or hydroxy.

6. A compound according to claim 5 which is (R)-N-(1-methyl-2-phenylethyl)-1-phenyl-6-propoxy-1H-pyrazolo-[3,4-d]pyrimidin-4-amine.

7. A compound according to claim 5 which is (S)-N-(1-methyl-2-phenylethyl)-1-phenyl-6-propoxy-1H-pyrazolo-[3,4-d]pyrimidin-4-amine.

8. A compound according to claim 5 which is [S-(R*,S*)]-α-[1-[(1-phenyl-6-propoxy-1H-pyrazolo[3,4-d-pyrimidin-4yl) amino]ethyl]benzeneethanol.

9. A compound according to claim 5 which is [R-(R*,S*)]-α-[1-[(1-phenyl-6-propoxy-1H-pyrazolo[3,4-d-pyrimidin-4yl) amino]ethyl]benzeneethanol.

10. A compound according to claim 5 which is (S)-β-[(1-phenyl-6-propoxy-1H-pyrazolo[3,4-d]pyrimidin-4-yl)-amino]benzenepropanol.

11. A compound according to claim 5 which is (R)-β-[(1-phenyl-6-propoxy-1H-pyrazolo[3,4-d]pyrimidin-4-yl)-amino]benzenepropanol.

* * * * *

UNITED STATES PATENT AND TRADEMARK OFFICE
CERTIFICATE OF CORRECTION

PATENT NO. : 5,256,650

DATED : October 26, 1993

INVENTOR(s) : Norton P. Peet, et al.

It is certified that error appears in the above-identified patent and that said Letters Patent is hereby corrected as shown below:

At column 3, line 66, the patent reads "from 1 to 3, " and should read --from 1 to 3 carbon atoms, and n is an integer from 1 to 3--.

At column 7, line 32, the patent reads "$10^{10-10}$ M to $10^4$ M" and should read --$10^{-10}$ M to $10^{-4}$ M--.

At column 8, line 31, the patent reads "$10^5$" and should read --$10^{-5}$--.

At column 8, line 58, in the table at number 9. under A-2, the patent reads ">6.99 x 10" and should read -->6.99 x $10^{-6}$--.

At column 9, line 12, the patent reads "2116-27" and should read --2117-28--.

At column 10, line 5, the patent reads "S-62-" and should read --S-$\beta$- --.

At column 10, line 8, the patent reads "S-8-" and should read -- S-$\beta$- --.

At column 11, line 4, the patent reads "d-propanol" and should read --n-propanol--.

At column 11, line 11, the patent reads "recrystalliza+tion" and should read --recrystallization--.

At column 11, lines 29- 30, the patent reads "1H-pyrazolo[3,4-d]pyrimidin-4pyrazolo[3,4-d]pyrimidin-4-amine" and should read --1H-pyrazolo[3,4-d]pyrimidin-4-amine--.

At column 11, lines 57 and 61, and at column 12, lines 4, 19 and 35, the patent reads "$\beta$" and should read --$\alpha$--.

At column 12, line 5, the patent reads "1H-pyrazolo[3,4-d]pyrazolo[3,4-dpyrimidin-4" and should read --1H-pyrazolo[3,4-d]pyrimidin-4--.

At column 12, line 6, the patent reads "136°-136°C" and should --136°-138°C--

At column 12, line 23, the patent reads "$\beta$-]" and should read -- $\alpha$-[ --

At column 12, line 25, the patent reads "benzenemethanol pyrimidin-4-yl)amino]ethyl]-benzenemethanol in 3 ml" and should read --benzenemethanol in 3 ml--.

UNITED STATES PATENT AND TRADEMARK OFFICE
CERTIFICATE OF CORRECTION

PATENT NO. : 5,256,650

DATED : October 26, 1993

INVENTOR(s) : Norton P. Peet, et al.

It is certified that error appears in the above-identified patent and that said Letters Patent is hereby corrected as shown below:

At column 12, line 46, the patent reads "ß" and should read --β-- .
At column 14, line 22, the patent reads "1H-yl)" and should read -- 1H-purin-6-yl) -- .
At column 14, line 30, the patent reads "(R)- β-[(9-(2,3,5-tri-O-acetyl]- β-D-ribofuranosyl)-2-chloro-1H" and should read --(R)- β-[(2-propoxy-9-(β-D-ribofuranosyl)-1H-- .
At column 16, line 56, claim 9, the patent reads "[R-(R*,S*)" and should read --[R-(S*,R*)--.

Signed and Sealed this

Fourth Day of May, 1999

Attest:

Q. TODD DICKINSON

*Attesting Officer*  Acting Commissioner of Patents and Trademarks